(12) United States Patent
Cohen et al.

(10) Patent No.: US 8,579,453 B1
(45) Date of Patent: Nov. 12, 2013

(54) DECORATIVE LIGHTING ASSEMBLIES UTILIZING SCENT RELEASING CARTRIDGES AND RELATED METHODS

(76) Inventors: Steven Martin Cohen, New York, NY (US); Gerald Cummings, Marlton, NJ (US); David Vogel, New York, NY (US)

( * ) Notice: Subject to any disclaimer, the term of this patent is extended or adjusted under 35 U.S.C. 154(b) by 0 days.

(21) Appl. No.: 13/357,071

(22) Filed: Jan. 24, 2012

(51) Int. Cl.
*F21V 19/02* (2006.01)

(52) U.S. Cl.
USPC ............... 362/96; 362/418; 362/482; 239/34

(58) Field of Classification Search
CPC ............ F21V 3/02; F21V 19/006; H01J 5/54; H01K 1/46
USPC ...................... 362/96, 235, 236, 441; 422/124
See application file for complete search history.

(56) References Cited

U.S. PATENT DOCUMENTS

| | | | |
|---|---|---|---|
| 1,706,939 | A | 3/1929 | Rosenthal |
| 2,468,164 | A | 4/1946 | Brewster et al. |
| 6,935,762 | B2 | 8/2005 | Van Dyn Hoven |
| 7,581,851 | B2 | 9/2009 | Wang |

FOREIGN PATENT DOCUMENTS

GB    1444204 B1    7/1976

*Primary Examiner* — Tracie Y Green
(74) *Attorney, Agent, or Firm* — David W Barman

(57) ABSTRACT

Fragrance-releasing cartridges for decorative illuminated assemblies of the type having an electrical cord terminated by at least one electrical connector, at least one lighting element, and at least one lighting element socket electrically coupled to the electrical cord and dimensioned and arranged to retain and make electrical contact with a corresponding lighting element. Each cartridge is formed from a molded polymer impregnated with a scented compound that is released at a substantially higher rate while heated by one of an associated lighting element and a discrete, resistive heating element.

17 Claims, 5 Drawing Sheets

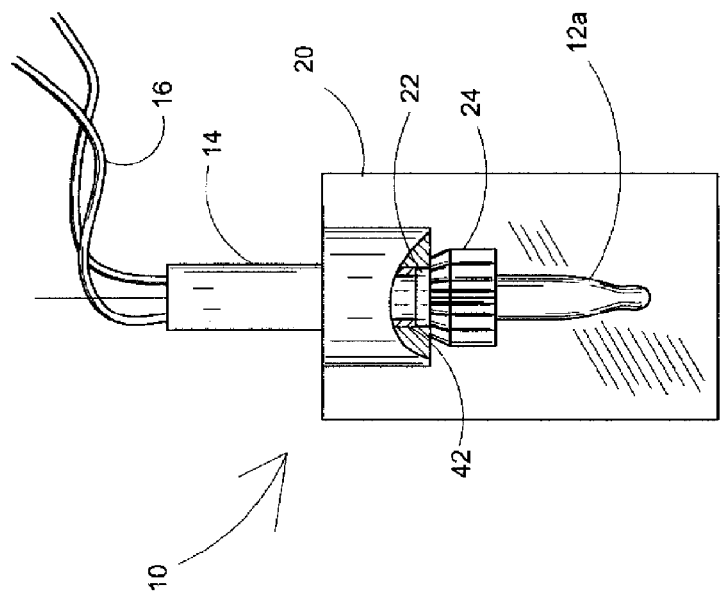
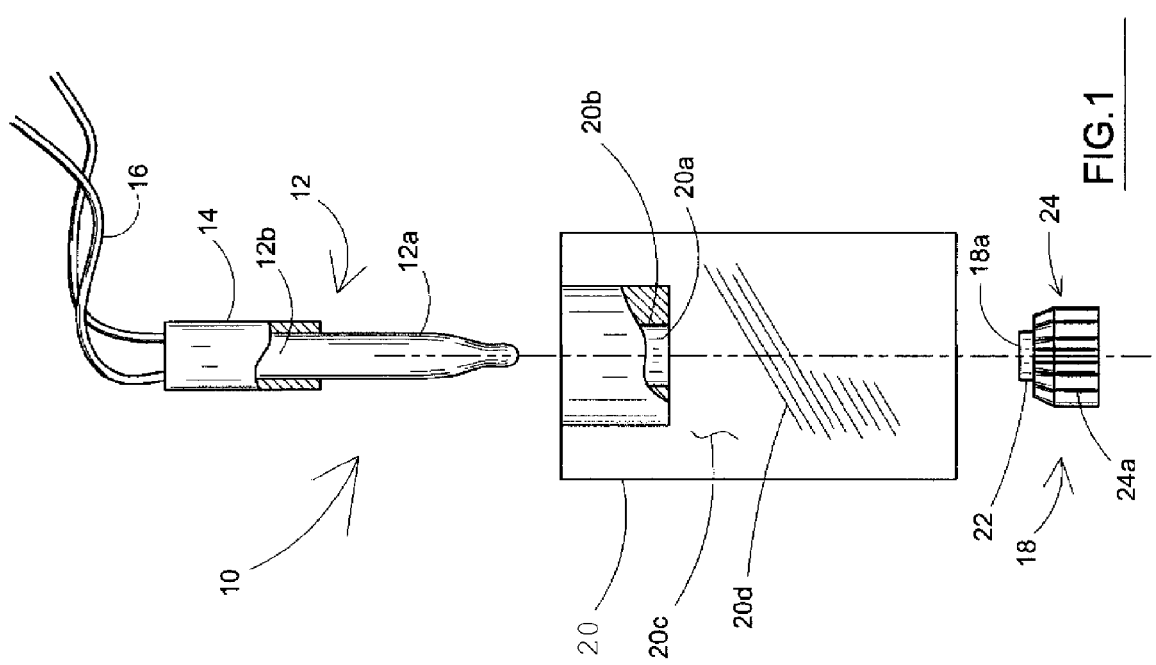

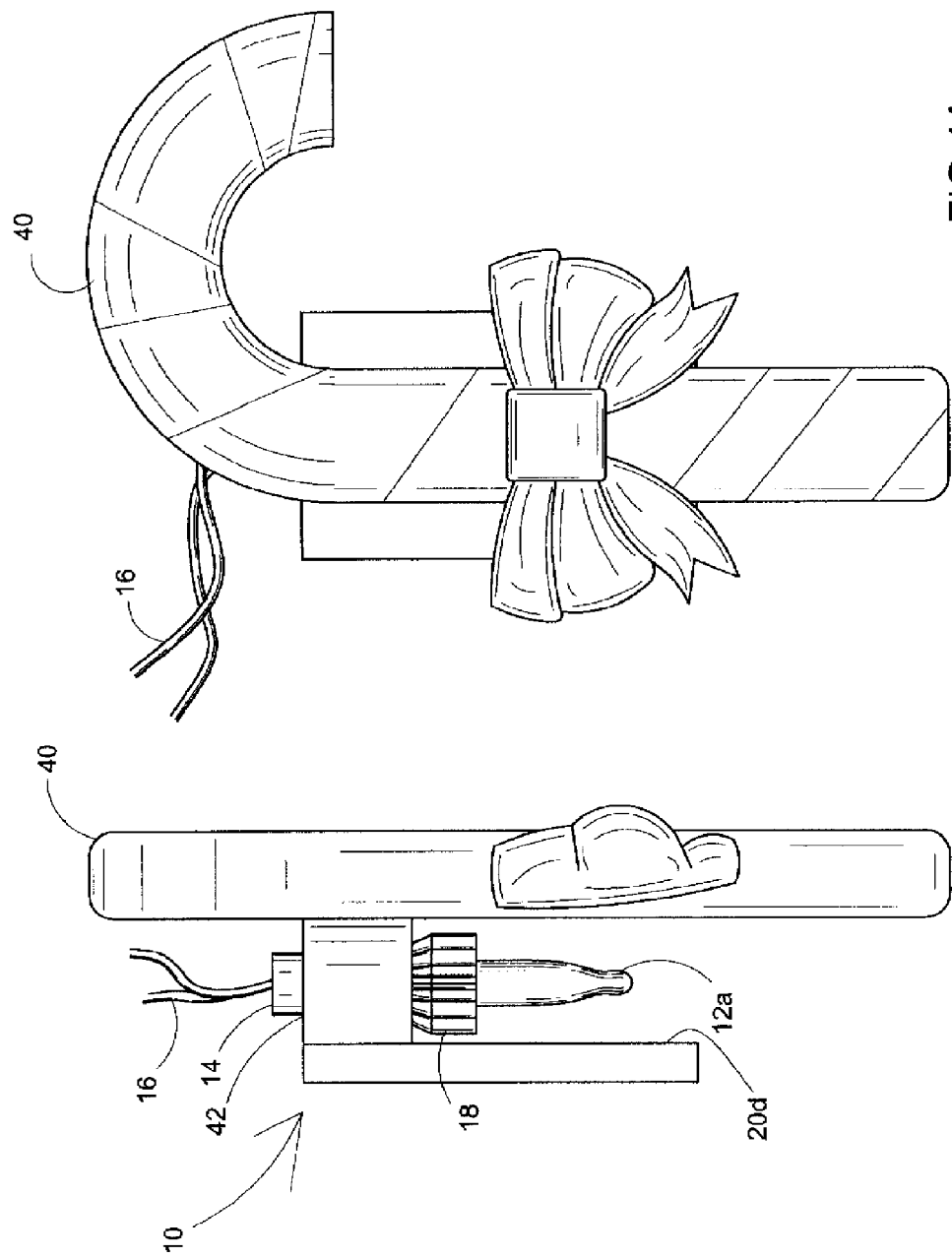

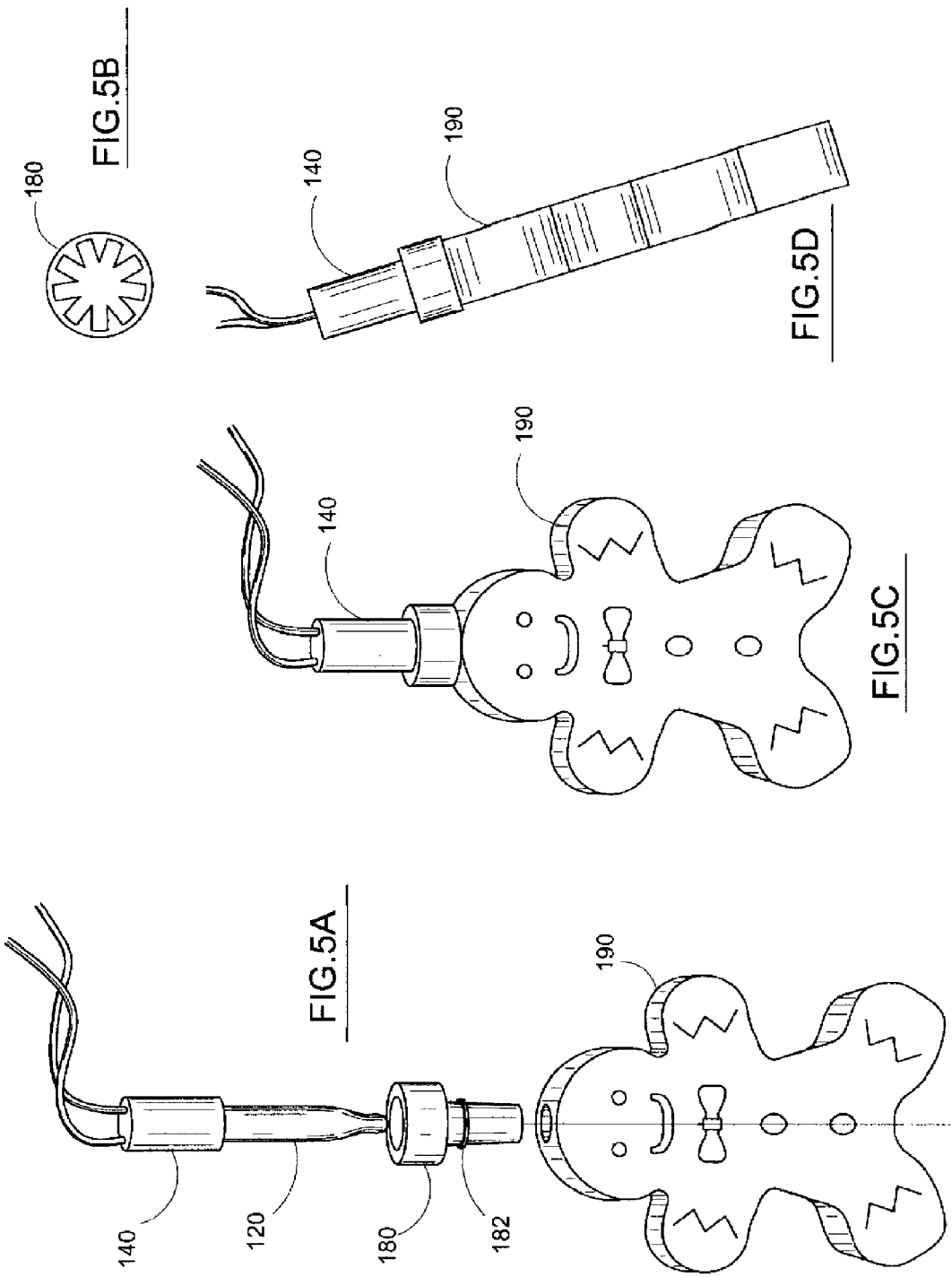

DECORATIVE LIGHTING ASSEMBLIES UTILIZING SCENT RELEASING CARTRIDGES AND RELATED METHODS

BACKGROUND

1. Field of the Invention

The present invention relates to electrical lighting and, more particularly, to the use of lighting elements in light strings and other decorative arrangements.

2. Discussion of the Prior Art

For many people, the act of decorating their homes and offices is a nostalgic tradition associated with the Christmas holiday season while for others it is a chance to express themselves creatively on select occasions. Decorative lights, whether arranged individually or in strings, are a particularly common sight during the holiday season. Decorative lights shaped as individual candles, for example, are used to provide a room with the aesthetics and ambience of an actual candle flame, but without the associated risk of fire or need for close attention. Light strings, on the other hand, are commonly used to adorn the family Christmas tree. Given the power of aromas like evergreen, cinnamon, vanilla, and other scents to evoke feelings of nostalgia and warmth during the holiday season, it is not surprising that various systems and techniques have been proposed to utilize the heat emitted by lighting elements, including those associated with decorative displays or light strings, to promote the distribution of such aromas.

For example, in U.S. Pat. No. 1,706,939 entitled "Evaporator" and issued to Rosenthal on Mar. 26, 1929, it is proposed to place an incandescent bulb within the cavity of a decorative, transparent assembly. Housed within the assembly is a container arranged to receive a volatile liquid such as a perfume and retain the liquid close enough to the light bulb to promote evaporation and thereby release a desirable fragrance into the surrounding area. In U.S. Pat. No. 2,468,164 entitled "Vaporizer" and issued to Brewster on Apr. 5, 1946, an annular liner adapted to surround a portion of an incandescent bulb proximate its base performs the same liquid retaining function as the container taught by Rosenthal, but provides a degree of isolation of the liquid in order to provide greater control of the rate of vaporization. Neither of these references are concerned with the release of seasonal fragrances corresponding to a holiday, holiday season, or festive occasion and, more importantly, the use of volatile liquids is simply not practical in the context of light strings and displays because the lighting elements have neither the physical shape nor the heat output required.

U.S. Pat. No. 6,935,762 issued to Van Dyn Hoven on Aug. 30, 2005 and entitled "Light String Assembly", along with UK Patent No. 1,444,204 issued to Miles on Jul. 28, 1976 and entitled "Clear Perfumed Polyamide Resin and Method of Making It" each disclose the concept of coating light emitting elements with a translucent, scent-bearing material such that a pleasing fragrance is released while the bulb(s) are illuminated. The principal disadvantages of this approach are that the complete encapsulation of the lighting elements results in a substantially shortened bulb life, and a release of fragrance that may be too rapid to last for an entire holiday season.

U.S. Pat. No. 7,581,851 issued to Wang on Sep. 1, 2009 and entitled "Scented Lighting Devices and Systems, and Methods for Making the Same" discloses a scented lamp holder structure which is dimensioned and arranged to establish electrical connectivity between the conductive leads of each lighting element and the light string wires. While the Wang lampholder structure does avoid the encapsulation issues associated with the Hoven and Miles arrangements, it is limited in its applicability to a specific light string configuration and, therefore, is not adaptable to the wide range of existing lighting strings and decorative light display configurations typically encountered in the commercial marketplace.

A continuing need therefore exists for decorative light assemblies and articles which retain the ability to release a scent for at least an entire holiday season.

A need also exists for decorative light assemblies and articles which incorporate a scent release structure which is not limited to any particular light string or decorative article configuration.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

The aforementioned needs are addressed, and an advance is made in the art, by a fragrance-releasing cartridge for use in decorative illuminated assemblies of the type having an electrical cord terminated by at least one electrical connector, at least one incandescent lighting element, and at least one lighting element socket electrically coupled to the electrical cord and dimensioned and arranged to retain and make electrical contact with a corresponding lighting element.

The cartridge may be configured with upper and lower sections wherein the lower section defines a first interior bore dimensioned and arranged to receive and retain an upper portion of a lighting element socket and the upper section defines a second interior bore axially aligned with the first interior bore and dimensioned and arranged to enclose at least a lower, light emitting portion of the first lighting element. Each cartridge is formed from a molded polymer impregnated with a scented compound that is released at a substantially higher rate while heated by, in accordance with some embodiments, an associated incandescent lighting element. Since light emitting diodes (LED's) can be used in decorative light strings, rather than incandescent lighting elements, it is contemplated by the inventors herein that alternate embodiments of the present invention may utilize discrete, electrically powered resistive heating elements to heat scent releasing cartridges.

Either or both of the first and section sections may be configured to contact, within the associated interior bore, corresponding surface portions of the socket and lighting element, respectively. By way of illustration, the first interior bore may be dimensioned and arranged to establish a close, friction fitting relationship between one or more interior surface portions of the cartridge and an exterior surface portion(s) of the lighting element socket, while the second interior bore may either be dimensioned and arranged with sufficient clearance to surround, but not contact the exterior surface portion(s) of the lighting element or to also establish a close, friction fitting relationship between one or more interior surface portions of the cartridge and exterior surface portion(s) of the lighting element.

In accordance with a modified embodiment of the invention, each cartridge may be configured to define an interior bore dimensioned and arranged to receive a light emitting portion of the first light emitting element, the modified cartridge being fabricated from a molded polymer incorporating both a scent releasing polymeric material.

To further promote the release of fragrance from fragrance releasing cartridges constructed in accordance with the present invention, the cartridge may be configured with exterior and/or interior protuberances such, for example, as radial fins so as to increase the amount of cartridge surface area exposed to ambient air.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DESCRIPTION OF THE DRAWINGS

FIG. 1 is an exploded view depicting a decorative, scented light assembly constructed using one or more scent releasing cartridges in accordance with an illustrative embodiment of the present invention;

FIG. 2 depicts the embodiment of FIG. 1 in a fully assembled condition;

FIG. 4A is a perspective view in elevation depicting a decorative, scent releasing light assembly in accordance with an embodiment of the present invention;

FIG. 4B is a partial, side elevation view illustrating the relationship between a scent releasing cartridge and the associated housing of the assembly of FIG. 4A;

FIG. 5A is an exploded view depicting a decorative, scented light assembly constructed using one or more scent releasing cartridges in accordance with another embodiment of the present invention;

FIG. 5B depicts a top view of the scent releasing cartridge utilized in the embodiment of FIG. 5A;

FIG. 5C depicts, in front elevation, the embodiment of FIG. 5A in a fully assembled condition; and FIG. 5D depicts, in side elevation, the embodiment of FIG. 5A in a fully assembled condition.

DETAILED DESCRIPTION

Figure 2A:
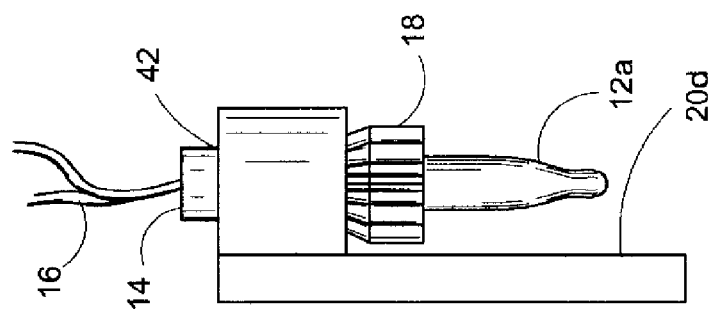
FIG. 2A is a side view from FIG. 2.

The present invention is directed toward devices and systems using electric lighting elements, light strings and lighted displays, and other lighted articles used not only to create a desired visual effect, but also to generate a desired scent during use, and to methods of making such devices and systems. The following is a detailed description of a few illustrative examples, the drawings being provided to clarify the description, and may not be to scale. Accordingly, and with particular reference now to FIG. 1, there is shown a decorative light assembly generally indicated at reference numeral 10 that is constructed in accordance with an illustrative embodiment of the present invention. Decorative light assembly 10 includes a lighting element 12 and a lighting element socket 14, which are coupled to a conductor 16 that terminates at one end in an electrical connector (not shown) such as a conventional plug insertable into a duplex receptacle or other source of electrical energy. Although only a single lighting element as lighting element 12 is shown in FIG. 1, it should be readily appreciated by those skilled in the art that incandescent bulb-based decorative light string embodiments of the invention will typically include ten to twelve or even more incandescent light bulb elements, depending principally upon the power requirements of the particular application (as will be explained in greater detail shortly). Each lighting element as lighting element 12 comprises an incandescent bulb 12a and base 12b. A pair of leads (not shown) on lighting element 12 are coupled to one or more wires in the conductor 16 via contacts (not shown) in socket 14, such that the bulb 12a illuminates when the conductor is energized.

In any event, and with simultaneous reference to FIGS. 1 and 2, it will be seen that decorative light assembly 10 further includes a scent releasing cartridge indicated generally at reference numeral 18 and an optional reflector housing indicated generally at reference numeral 20. In the exemplary embodiment of FIG. 1, cartridge 18 has a single section defining an interior bore 18a dimensioned and arranged to enclose a portion of bulb 12a when the latter is inserted into the position depicted in FIG. 2. Reflector housing 20 defines an interior bore indicated generally at reference numeral 20a and is dimensioned and arranged to receive and retain socket 14 as depicted in FIG. 2. The diameter of interior bore 20a may, for example, be selected so as to achieve a friction-fitting relationship with socket 14. It should be noted, however, that any suitable means may be used to couple the reflector housing to socket 14. Thus, for example, socket 14 may instead be adhesively or mechanically bonded to the interior surface 20b of reflector housing 20. Extending from reflector base 20c is a reflective section 20d configured, by way of illustration, as a Mylar-coated, arcuate shroud. However, the reflector can be made of any reflective material, including but not limited to Mylar.

Figure 3A:
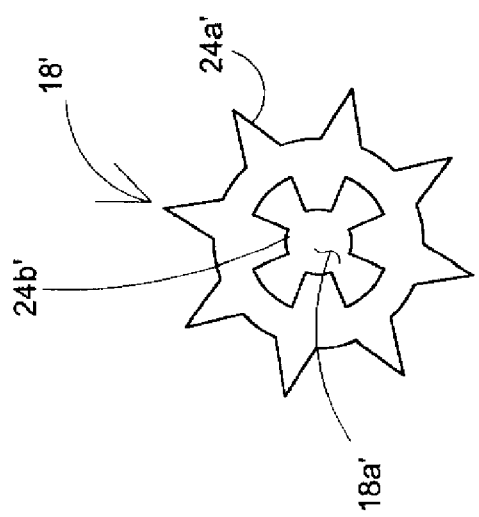
FIG. 3A depicts, in top plan view, an illustrative configuration of a scent releasing cartridge constructed in accordance with the present invention.
Figure 3B:
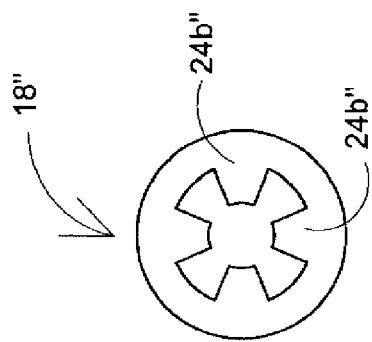
FIG. 3B depicts, in top plan view, an alternative configuration of a scent releasing cartridge constructed in accordance with the present invention.

With continued reference to FIGS. 1 and 2, it will be seen that scent releasing cartridge 18 includes a proximal portion indicated generally at 22 dimensioned and arranged for frictional fitting relation within interior bore 20a of reflector housing 20. A distal portion of cartridge 18 indicated generally at reference numeral 24 includes a plurality of radially extending protuberances or fins 24a. FIG. 3A depicts an alternate cartridge embodiment 18' in which protuberances 24a' are formed not only on the exterior surface of the cartridge, but also within the interior bore 18a'. Such an arrangement presents a larger surface area for evaporization of the scented material present in cartridge 18' into the atmosphere and, in those embodiments where interior surfaces of cartridge 18' are maintained in contact with the heated, light transmitting surfaces of bulb 12a. FIG. 3B depicts yet another cartridge configuration in which cartridge 18" incorporates only internally directed fins.

Figure 3C:
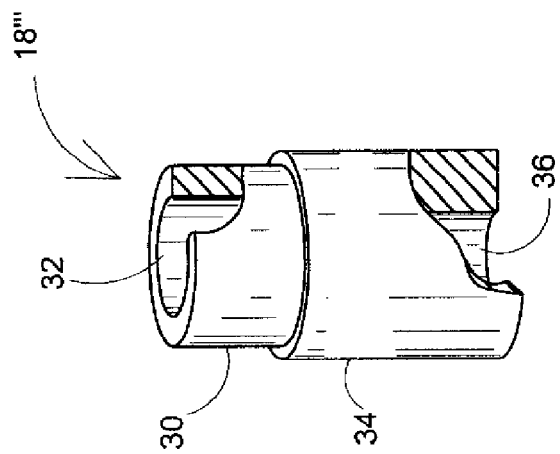
FIG. 3C is a perspective view in elevation showing yet another exemplary configuration of a scent releasing cartridge constructed in accordance with the present invention.

Returning briefly to FIGS. 1 and 2, it should be noted that reflector 20 may be omitted in its entirety, in which case cartridge 18 may be implemented using the exemplary configuration 18''' shown in FIG. 3C. Cartridge 18''' comprises a first section indicated generally at 30 that defines an interior bore 32 dimensioned and arranged to receive and retain a portion of socket 14 in, for example, friction fitting arrangement. Cartridge 18''' further includes a second section indicated generally at 34 that defines an interior bore dimensioned and arranged to receive and enclose at least a portion of bulb 12a (FIGS. 1 and 2).

FIGS. 4A and 4B depict another example of a decorative light assembly having a translucent housing that defines a mounting hole 42 for receiving either socket 14 or socket 14 and a portion of a scented cartridge 18 constructed in the manner exemplified by FIG. 1 or any of FIGS. 3A-3C. In the latter case, cartridge 18 defines an interior bore dimensioned and arranged such that cartridge 18 contacts the exterior surface of bulb 12a. When energized, bulb 12a illuminates the translucent portion of housing 14 while simultaneously releasing a scent associated with the shape of the housing. In the illustrative examples of FIG. 4A and FIG. 4B, the housing 40 is in the form of a candy cane and the scent released through heating of cartridge 18 is selected to be a peppermint scent. Alternative examples include a housing 40 having a pine tree shape matched with a pine-scented cartridge, and a gingerbread man shape matched with a ginger-scented cartridge.

Turning now to FIGS. 5A-5D, there is shown an alternative embodiment of the present invention. With initial reference to FIG. 5A, it will be seen that a scent releasing cartridge indicated generally at 180 is dimensioned and arranged to fit over a light emitting element 120 received within holder 140. Scent releasing cartridge 180 is dimensioned and arranged for insertion into an aperture within a decorative article such as the gingerbread-man shaped article indicated generally at reference numeral 190. The scent released by cartridge 180 is selected so as to correspond to the decorative article in which it is inserted which, in the illustrative case, is the aroma of gingerbread. Cartridge 180 is preferably fabricated from an elastomeric material and may be provided with an interior profile such as that shown in FIG. 5B to both maximize the surface area of scented material exposed to the heat emitting surface of lighting element 120 and provide convective air channels to enhance the flow of scented air. A peripheral lip 182 helps retain cartridge 180 in the seated condition depicted in FIGS. 5C and 5D. Decorative article 190 is preferably fabricated from a translucent material so as to allow it to be illuminated by lighting element 120.

When lighting elements such as elements 120 are of the light emitting diode type, rather than of the heat-emitting, incandescent type, it is necessary to provide an alternative means of heating the scent releasing cartridges as cartridge 180. By way of illustrative example, a resistive heating element (not shown) may be juxtaposed between holder 140 and lighting element 120. The provision of an appropriate adapter suitable to such purpose is deemed by the inventors herein to be within the level of skill of the ordinary artisan and, for this reason, a detailed description and illustration of the same has been omitted for clarity.

In each of the above-described embodiments, the device or system incorporates a cartridge made from a material that generates a significant amount of a desired scent when the lighting element, light string or lighted display is operating, but does not generate as much of the scent when the same is not operating. The concentration of the scented compound is selected such that the rate at which scent is generated at the operating temperature of all energized bulb(s) 12a is at or above the concentration sufficient for individuals in the vicinity of the lights to readily appreciate the scent while the rate at which scent is generated by all bulb(s) 12 at room temperature is below the concentration necessary for individuals in the vicinity of the lights to readily appreciate the scent.

Example 1

The inventor has practiced the present invention in several different ways, and provides herein a representative example of a method used to manufacture a scented device according to the present invention. In this particular example, the inventor used at least the following compounds: fragrant grains obtained by dipping 30-35% by weight of homologous microporous plastic material in 65-70% by weight of fragrant oil of high boiling point and low viscosity for about 24 hours, the homologous microporous plastic material having open cells in it. The fragrant grains were mixed with a silicone solventless resin, such as SYLGUARD 186 (available from Dow Corning Corp., Midland Mich.) at a ratio of 10% by weight of fragrant grains and 90% by weight of resin, forming a translucent, injection moldable material that can be allowed to cure at room temperature mixed with 9 parts to 1 with its curative.

Example 2

The inventor has practiced the present invention in several different ways, and provides herein another representative example of a method used to manufacture a scented device according to the present invention. In this particular example, the inventor used at least the following compounds: a resin, a fragrance diluter, a dispersing agent, a fragrance, a fragrance main agent, and an anti-oxidant. The procedure including the steps of: adding the fragrance to the fragrance diluter and stirring thoroughly; mixing in the dispersing agent, the anti-oxidant and the resin; and melting the propylene pellets from an injection machine at a temperature between 80-120 degrees Celsius, the ratio of polypropylene and fragrance main agent mix being between about 8:1 to about 12:1 by weight. The pellets are then used to produce product by injection as generally understood in the art. An individual of ordinary skill in the art having reviewed this disclosure will appreciate that these compounds, ratios, temperatures and/or steps can be changed or supplemented without deviating from the spirit of the invention.

Though the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A decorative assembly, comprising:
   an electrical cord terminated by at least one electrical connector;
   a first lighting element;
   a first lighting element socket electrically coupled to the electrical cord and dimensioned and arranged to retain and make mating electrical contact with the first lighting element; and
   a fragrance releasing cartridge coupled to at least one of the first lighting element socket and the first lighting element, said cartridge having at least one of a first section defining an interior bore dimensioned and arranged to receive and retain an upper portion of the first lighting element socket and a second section defining an interior bore dimensioned and arranged to enclose at least a lower, light emitting portion of the first lighting element, wherein the cartridge is made from a material comprising a scented compound having a desired scent, the scented compound being present throughout the cartridge and having an elevated rate of vaporization from the material when the cartridge is in a heated state due to being in close proximity to one of an illuminated, heat producing lighting element and a discrete, resistive heating element, the elevated rate of vaporization being significantly greater than a reduced rate of vaporization of the scented compound from the material when the cartridge is not in the heated state and further wherein the cartridge includes the first and second sections, the interior bore of the first section being dimensioned and arranged to retain the upper portion of the first lighting element socket in a friction fitting relationship, whereby the cartridge may be removed and replaced after substantially all of the scented compound evaporates.

2. The assembly of claim 1, further including a second lighting element, a second lighting element socket electrically coupled to the electrical cord and dimensioned and arranged to retain and make mating electrical contract with the second lighting element, and a second fragrance releasing cartridge coupled to the second lighting element socket.

3. The assembly of claim 1, wherein the cartridge includes the second section, the second section defining an outer surface having a plurality of protuberances extending radially therefrom to provide an increased surface area for heat transfer and evaporation of the scented compound.

4. The assembly of claim 3, wherein the second section further defines an interior surface having a plurality of protuberances extending inwardly into the interior bore of the second section to thereby provide an increased surface area for heat transfer and evaporation of the scented compound.

5. The assembly of claim 1, wherein the cartridge includes the second section, the second section defining an interior surface having a plurality of protuberances extending inwardly into the interior bore of the second section to thereby provide an increased surface area for heat transfer and evaporation of the scented compound.

6. The assembly of claim 1, further including a housing having a shape representative of one of a pine tree, a candy cane, a gingerbread man, and another distinctive shape having a correspondingly distinct identifying aroma associated therewith, said housing including a translucent portion aligned with a mounting opening dimensioned and arranged to receive at least the upper section of the cartridge, whereby the first incandescent lighting element provides illumination of at least the translucent portion.

7. An article for use in a decorative illuminated assembly having an electrical cord terminated by at least one electrical connector, at least one incandescent lighting element, and at least one lighting element socket electrically coupled to the electrical cord and dimensioned and arranged to retain and make electrical contact with a corresponding incandescent lighting element, a fragrance releasing cartridge article comprising at least one of:
a first section defining a first interior bore dimensioned and arranged to receive and retain an upper portion of a lighting element socket; and
a second section defining a second interior bore dimensioned and arrange to enclose at least a lower, light emitting portion of a lighting element retained in a lighting element socket, wherein the cartridge is made from a material comprising a scented compound having a desired scent, the scented compound being present throughout the cartridge and having an elevated rate of vaporization from the material when the cartridge is in a heated state due to being in close proximity to one of an illuminated, heat producing lighting element and a discrete, resistive heating element, the elevated rate of vaporization being significantly greater than a reduced rate of vaporization of the scented compound from the material when the cartridge is not in the heated state, and further wherein the cartridge includes the first and second sections, the interior bore of the first section being dimensioned and arranged to retain the upper portion of the first lighting element socket in a friction fitting relationship, whereby the cartridge may be removed and replaced after substantially all of the scented compound evaporates.

8. The article of claim 7, the article including both the first section and the second section and wherein the first interior bore is axially aligned with the second interior bore.

9. The article of claim 8, wherein the first interior bore of the cartridge is dimensioned and arranged to retain the upper portion of a corresponding lighting element socket in a friction fitting relationship, whereby the cartridge may be removed and replaced.

10. The article of claim 8, wherein the second section of the fragrance releasing cartridge defines an outer surface having formed thereon a plurality of outwardly extending protuberances to provide an increased surface area for heat transfer and evaporation of the scented compound.

11. The article of claim 10, wherein the second section of the fragrance releasing cartridge further defines an interior surface having formed thereon a plurality of protuberances extending inwardly into the second interior bore to provide an increased surface area for heat transfer and evaporation of the scented compound.

12. The article of claim 8, wherein the second section of the fragrance releasing cartridge defines an interior surface having formed thereon a plurality of protuberances extending inwardly into the second interior bore to provide an increased surface area for heat transfer and evaporation of the scented compound.

13. The article of claim 8, further including a housing having a shape representative of one of a pine tree, a candy cane, and a gingerbread man, said housing including a translucent portion aligned with a mounting opening dimensioned and arranged to receive at least the upper section of the cartridge, whereby the first incandescent lighting element provides illumination of at least the translucent portion.

14. The article of claim 7, further including a thermal conductivity enhancer present in an amount sufficient to increase the thermal conductivity of the cartridge.

15. The article of claim 14, wherein the cartridge is fabricated from a translucent elastomeric material and wherein the thermal conductivity enhancer is a thermally conductive nanopowder.

16. A decorative light string assembly, comprising:
an electrical cord terminated by at least one electrical connector;
a plurality of lighting elements;
a plurality of lighting element sockets each electrically coupled to the electrical cord and dimensioned and arranged to retain and make mating electrical contact with a corresponding one of the plurality of lighting elements; and
a plurality of fragrance releasing cartridges each coupled to a corresponding one of the lighting element sockets, each said cartridge having at least one of a first section defining a first interior bore dimensioned and arranged to receive and retain an upper portion of a corresponding lighting element socket and a second section defining a second interior bore dimensioned and arranged to enclose at least a lower, light emitting portion of a corresponding lighting element, wherein each cartridge is made from a material comprising a scented compound having a desired scent, the scented compound being present throughout each cartridge and having an elevated rate of vaporization from the material when each cartridge is in a heated state due to being in close proximity to one of an illuminated lighting element and a heat-producing resistive element, the elevated rate of vaporization being significantly greater than a reduced rate of vaporization of the scented compound from the material when a cartridge is not in the heated state, wherein each cartridge includes both the first and second sections, the second section of each cartridge defining an outer surface having a plurality of protuberances extending radially therefrom to provide an increased surface area for heat transfer and evaporation of the scented compound.

17. The assembly of claim 16, wherein the cartridge includes the second section, the second section defining a plurality of protuberances extending inwardly into the second interior bore to thereby provide an increased surface area for heat transfer and evaporation of the scented compound.

\* \* \* \* \*